United States Patent [19]

Klaveness et al.

[11] Patent Number: 5,767,299

[45] Date of Patent: Jun. 16, 1998

[54] CONTRAST AGENTS

[75] Inventors: Jo Klaveness; Per Strande, both of Oslo, Norway

[73] Assignee: Nycomed Imaging AS, Oslo, Norway

[21] Appl. No.: 507,296

[22] PCT Filed: Feb. 25, 1994

[86] PCT No.: PCT/GB94/00375

§ 371 Date: Sep. 18, 1995

§ 102(e) Date: Sep. 18, 1995

[87] PCT Pub. No.: WO94/19025

PCT Pub. Date: Sep. 1, 1994

[30] Foreign Application Priority Data

Feb. 26, 1993 [GB] United Kingdom ............... 9303992

[51] Int. Cl.$^6$ .................................................. C07C 59/00
[52] U.S. Cl. ...................... 554/220; 424/9.4; 424/9.45; 424/9.451; 554/223; 554/227; 554/225; 554/226
[58] Field of Search ..................... 554/523, 220, 554/225, 227, 226; 424/9.4, 9.45, 9.451

[56] References Cited

U.S. PATENT DOCUMENTS 4,567,034  1/1986  Charles et al.

FOREIGN PATENT DOCUMENTS

| A-0 153 992 | 9/1985 | European Pat. Off. |
| A-0 436 316 | 7/1991 | European Pat. Off. |
| A-0 498 482 | 8/1992 | European Pat. Off. |
| A-0543 454 | 5/1993 | European Pat. Off. |
| WO-A-91 12231 | 8/1991 | WIPO |

OTHER PUBLICATIONS

*Patent Abstracts of Japan*, vol. 013, No. 236 (C–602) 30 May 1989.
*Chemical Abstracts*, vol. 110, No. 25, 19 Jun. 1989, 231292c.
*DATABASE WPI*, Section Ch, Week 8944, Derwent Publications Ltd., London.
*Chemical Abstracts*, vol. 114, No. 7, 18 Feb. 1991, 61709g.
Wolff, M.E., Ed., *Burger's Medicinal Chemistry*, 4th ed., part 3, 1979, 1147–1203.

*Primary Examiner*—Gary Geist
*Assistant Examiner*—Deborah D. Carr
*Attorney, Agent, or Firm*—Bacon & Thomas

[57] ABSTRACT

The invention relates to compounds of formula (I):

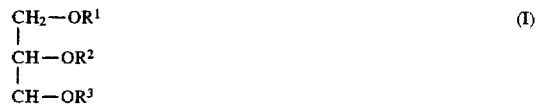

wherein $R^1$, $R^2$ and $R^3$ are independently selected from:

(i) saturated or unsaturated fatty acyl groups, preferably having from 14 to 24 carbon atoms, more preferably of a type found in nature; or (ii) groups of formula (II):

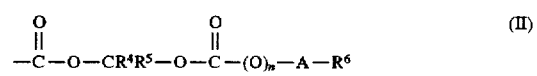

wherein $R^4$ and $R^5$ are independently selected from hydrogen atoms, $C_{1-4}$alkyl groups and aryl groups, preferably $C_{6-10}$aryl groups; n represents the integers 0 or 1; A represents either a chemical bond or a straight or branched $C_{1-6}$alkylene chain and $R^6$ is a triiodinated phenyl group which may also carry other substituents. The invention also relates to X-ray contrast media containing these compounds, as well as methods of enhancing X-ray images of a human subject wherein the contrast media are administered to the subject prior to imaging.

15 Claims, No Drawings

5,767,299

1

CONTRAST AGENTS

This application is a 371 of PCT/GB94/00375 filed Feb. 25, 1994.

This invention relates to X-ray contrast agents.

It has been proposed to improve the detection of lesions in the liver and spleen by the use of contrast agents which accumulate in these organs. A useful survey entitled "Particulate Suspensions as Contrast Media" can be found in Radiocontrast Agents (Handbook of Experimental Pharmacology vol. 73), ed. M. Sovak, pub. Springer Verlag Berlin/Heidelberg, 1984 at page 543. The authors report on the use of inorganic particulate contrast media, organic particulate contrast media and emulsified contrast media.

Of the inorganic particulate contrast media the most well known is thorium dioxide. Use of this medium has been discontinued because of its chronic toxicity.

Organic particulate contrast media have included various iodinated compounds preferably containing three or more iodine atoms to maximise opacity, attached to an aromatic ring for chemical stability. However, compounds such as the ethyl esters of iodipamide and iothalamate are not sufficiently metabolically labile and would be expected to be retained in the liver for some time (see also Violante et. al., Investigative Radiology 16, pages 40–45, 1981).

Other organic particulate contrast media have been proposed in WO89/00988 and WO90/07491 with a view to overcoming the difficulties experienced with earlier organic media.

Emulsified contrast media in general comprise iodinated lipids such as iodinated poppyseed oil. A major disadvantage is that the iodine is aliphatic and hence more chemically reactive, particularly towards blood components.

Another possibility is to use liposomes containing water soluble iodinated contrast agents (Havron et al., Radiology, 140, p. 507, 1981). However, since only a limited amount of iodine can be incorporated in each liposome, it is necessary to administer relatively large amounts of lipids in order to attain adequate contrast enhancement. This tends to cause emboli in the lung capillaries. Furthermore, liposomes have been found to be relatively unstable on storing (Shulkin et al., J. Microencapsul., 1, p. 73, 1984).

Cholesteryl iopanoate has been proposed as a lipid-soluble contrast agent (Longino et al., Investigative Radiology 18, pages 275–278, 1983). However the compound has too long a liver retention time for human use.

Contrast agents based on the naturally occurring lipid triglyceride structure have been proposed in U.S. Pat. Nos. 4,873,075, 4,957,729 and 5,093,042 of Counsell et al. However, compounds of this type do not achieve a good enough rate of degradation within the body, and/or an acceptable rate of excretion from the body.

It has now been found according to the present invention that triglyceride-based contrast agents possessing a rapidly enzymatically degradable group between the glycerol backbone and the iodinated moiety possess advantages of good biodegradation to products of low toxicity which may be rapidly excreted from the body following imaging. The biodegradable groups are rapidly degraded in vivo by esterase enzymes but are stable in the absence of such enzymes.

Accordingly a first aspect of the invention provides compounds of formula (I)

2

$$\begin{array}{l} CH_2-OR^1 \\ | \\ CH-OR^2 \\ | \\ CH_2-OR^3 \end{array}$$

wherein $R^1$, $R^2$ and $R^3$ are independently selected from:
(i) saturated or unsaturated fatty acyl groups, preferably having from 14 to 24 carbon atoms, more preferably of a type found in nature;
(ii) groups of formula $$-\overset{O}{\underset{\|}{C}}-O-CR^4R^5-O-\overset{O}{\underset{\|}{C}}-(O)_n-A-R^6$$

wherein $R^4$ and $R^5$ are independently selected from hydrogen atoms, $C_{1-4}$ alkyl groups and aryl groups, preferably $C_{6-10}$ aryl groups, n represents the integers 0 or 1, A represents either a chemical bond or a straight or branched $C_{1-6}$ alkylene chain and $R^6$ is a group

[phenyl ring with substituents $R^7$, $R^8$, $R^9$, $R^{10}$, $R^{11}$]

wherein at least three of $R^7$, $R^8$, $R^9$, $R^{10}$ and $R^{11}$ are iodine atoms and those of said groups $R^7$, $R^8$, $R^9$, $R^{10}$ and $R^{11}$ which are not iodine atoms are selected from hydrogen atoms, halogen atoms other than iodine, hydroxyl groups, $C_{1-6}$ alkoxy groups, amino groups, $C_{1-6}$ alkylthio groups, N-($C_{1-6}$ alkyl)-amino groups, N-($C_{1-6}$ alkanoyl)-amino groups, N-($C_{1-6}$ alkyl)-N-($C_{1-6}$ alkanoyl)-amino groups, carbamoyl groups and N-($C_{1-6}$ alkyl)-carbamoyl groups, wherein any of the alkyl, alkylene, alkoxy, alkylthio, N-alkyl or N-acyl groups defined above may be substituted by one or more hydroxy or $C_{1-4}$ alkoxy groups, preferably one or two such groups;

provided that at least one of $R^1$, $R^2$ and $R^3$ is a fatty acyl group and at least one of $R^1$, $R^2$ and $R^3$ is a radical containing an iodinated phenyl group as defined above.

It is particularly preferred that the iodinated phenyl groups in the radicals of the type (ii) are 2,4,6-triiodophenyl groups since these are of proven safety and efficacy in both ionic and non-ionic contrast media.

The preferred meanings for those of $R^7$, $R^8$, $R^9$, $R^{10}$ and $R^{11}$ which are not iodine are hydrogen, hydroxyl, $C_{1-6}$alkoxy, amino, N-($C_{1-6}$alkanoyl)-amino, N-($C_{1-6}$alkyl)-N-($C_{1-6}$alkanoyl)-amino, carbamoyl and N-($C_{1-6}$alkyl)-carbamoyl.

It is particularly preferred that those of the groups $R^7$, $R^8$, $R^9$, $R^{10}$ and $R^{11}$ which are not iodine atoms are acylamino groups of formula $$-N(Ac)R^{12}$$

where Ac is $C_{1-6}$ alkanoyl such as acetyl or a hydroxy-substituted alkanoyl group while $R^{12}$ is hydrogen or a $C_{1-6}$ alkyl group such as methyl or a hydroxy-substituted alkyl group.

Alternatively carbamoyl groups of formula $$-CONR^{13}R^{14}$$

wherein $R^{13}$ and $R^{14}$ are hydrogen, $C_{1-6}$ alkyl or hydroxy-substituted alkyl groups are also particularly preferred.

The group A preferably represents a methylene or ethylene chain.

The compounds wherein n represents the integer 0 and A represents a chemical bond, that is where

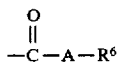

is a benzoic acid moiety, are especially preferred.

When $R^1$, $R^2$ or $R^3$ is a fatty acyl group this is most preferably derived from a $C_{16-18}$ fatty acid, for example palmitic acid, stearic acid and in particular oleic acid.

The compounds according to the invention are suitably prepared by processes forming a further aspect of the invention, namely (a) acylation of a compound of formula (Ia)

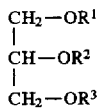  (Ia)

in which $R^1$, $R^2$ and $R^3$ represent either hydrogen atoms or groups as defined above for formula (I), with the proviso that at least one of $R^1$, $R^2$ and $R^3$ is a hydrogen atom;

(b) reaction of a compound of formula (Ib)

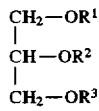  (Ib)

wherein $R^1$, $R^2$ and $R^3$ either represent groups of formula (II)

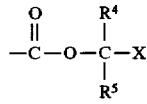  (II)

wherein $R^4$ and $R^5$ are as defined above for formula (I) and X is a leaving group such as a halogen atom (for example chlorine) or a mesyloxy or tosyloxy group, or $R^1$, $R^2$ and $R^3$ represent fatty acyl groups as defined above for formula (I) (provided that at least one of $R^1$, $R^2$ and $R^3$ is a fatty acyl group and at least one of $R^1$, $R^2$ and $R^3$ is a group of formula (II) as defined above) with a compound serving to introduce the group

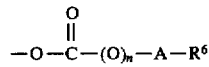

wherein n, A and $R^6$ are as defined for formula (I).

The compounds of formula (Ib) are themselves new and form an additional aspect of the invention. Although of particular use in the preparation of compounds of formula (I), they will also have other utilities such as in the synthesis of other pharmaceuticals or contrast agents based on readily biodegradable triglycerides. They may be prepared by reaction of a compound of formula (Ia) as defined above with a haloalkyl haloformate of formula

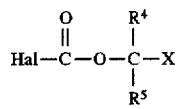

wherein Hal is a halogen atom, for example a chlorine atom, $R^4$ and $R^5$ are as defined above and X is as defined above.

In the production of compounds of formula (I) from compounds of formula (Ia) as defined above, the acylating agent may be any of the types of acylating agent known to those in the art, for example an acid halide or acid anhydride or an activated ester such as a succinimide ester. Acylation may also be performed using an acid in the presence of a coupling agent such as a carbodiimide.

Where the compounds of formula (I) are to be produced by reaction of a compound of formula (Ib), the co-reactant serving to introduce the group

is suitably a salt of the corresponding carboxylic acid, for example a potassium or cesium salt, the reaction conveniently being catalysed by potassium or cesium iodide.

The compounds are conveniently formulated as a suspension or emulsion with particle/droplet sizes in the range 0.01–10 μm. They may be prepared by stirring, sonication, homogenization and other known methods. Particles of the compounds may be suspended in a medium with suitable stabilisers, or for compounds with a lower melting point or a greater solubility in hydrophobic solvents droplets of pure compound or of compound dissolved in a solvent may likewise be suspended in a medium with suitable stabilisers. Examples of stabilisers are anionic, cationic, zwitterionic and non-ionic surfactants, including lipid molecules, used alone or in combination. Lipophilic co-surfactants with a low HLB value may be added to improve the stability, surface charge, viscosity, elasticity or membrane permeability of the suspension. Biodegradability can be improved by suitable choice of surfactant, circulation time within the body may be adjusted and it may also be possible to reduce any toxic side-effects which are present. Other types of stabiliser include linear or branched polymers, linear or branched copolymers such as block and graft copolymers, polyelectrolytes and proteins.

A preferred formulation of the compounds is to dissolve them in biologically acceptable hydrophobic liquids such as liquid triglycerides or fluorinated compounds such as perfluorooctylbromide or perfluorodecalin, in order to obtain solid compounds as a liquid phase or, where the compounds are liquid at room temperature, to alter the viscosity or other physical properties such as emulsion stability. In this manner, the compounds may be formulated as an emulsion with droplet size in the range 0.1 to 5 μm, by the above mentioned techniques and optionally including the above-mentioned stabilizers, and administered as a chylomicron-like emulsion.

As an aid to the emulsification process, volatile solvents such as ethers, chlorinated hydrocarbons, perfluorohydrocarbons, aliphatic or cycloaliphatic or aromatic hydrocarbons, short chain alcohols, aldehydes, ketones or other solvents such as dimethyl-sulphoxide, tetrahydrofuran or dimethylformamide may be used. Emulsification may take place using the above mentioned techniques, followed by removal of the hydrophobic solvent by a vaporization method, freeze drying or spray drying. The final particles may be redispersed in an aqueous medium.

A fine particle suspension of compounds which are solid at room temperature may be prepared by dissolving the compound in a suitable solvent and by spray drying the compound, obtaining a fine powder of the pure compound. Alternatively, the compound may be formulated as an emulsion with the above mentioned techniques, and spray dried in order to obtain fine particles. The particles may be dissolved in an aqueous medium optionally with added stabilizers, obtaining a fine suspension with the preferred size range between 0.1 and 5 µm.

Preferred stabilizers are surfactants and lipids such as salts of fatty acids with 6 to 30 carbon atoms in the chain, and with varying degrees of saturation, carbon chain branching, etc.; sulphates and sulphate esters of the fatty acids above; cationic surfactants such as quaternary ammonium salts with one or two hydrocarbon chains with length between 4 and 30 carbon atoms, and with varying degrees of saturation and branching; surfactants such as esters or ethers of fatty acids or fatty alcohols with polyoxyethylene compounds; ethers of fatty acids with polyoxyalkylated sorbitan or glycol; polyethoxylated soya oil and castor oil; and esters or ethers of carbohydrates with fatty acids or fatty alcohols, for instance polyoxyalkylated mono-, di- and triglycerides of saturated or unsaturated fatty acids, glycerides of soya oil and sucrose. Preferred are also phospholipids such as for instance egg or soyabean lecithin, or synthetic lecithins such as alkylphosphatidyl cholines, alkyl phosphatidyl ethanolamines, alkyl phosphoglycerols and so on. Preferred cosurfactants may be substances such as for instance fatty acids, fatty alcohols or fatty amines with straight or branched hydrocarbon chains and with varying degrees of saturation, with 4 to 30 carbon atoms in the chain, or sterols such as cholesterol and the like. Polymers or polyelectrolytes such as heparin, hyaluronic acid, polyethylene oxide, polypropylene oxide, polylactides, polyglycolides or other polysaccharides, and graft or block copolymers of these, for instance poloxamers, may also be used. Proteins such as albumins, gelatins, collagen and globulins may also be used. The use of synthetic proteins may be preferred in order to avoid allergenic reactions in vivo.

Especially preferred formulations use compounds according to the invention which are in a liquid state at room temperature, where a chylomicron-like emulsion may be formulated by the above mentioned methods without any hydrophobic liquid additives, thus retaining the high density of radiopaque active iodine groups. A fine emulsion which can be administered in low doses as measured by particle volume or interface area can be obtained.

Especially preferred are also formulations using compounds according to the invention which have a relatively low melting point making it possible to prepare chylomicron-like oil-in-water emulsions without any additives other than the stabilizers, by heating the substances in water to the melting point, if necessary also by applying pressure. The fine emulsion obtained may in turn be cooled, obtaining particles coated with the stabilizer, with high density of the radiopaque active iodine groups. A fine emulsion which can be administrated in relatively low doses can be obtained.

Especially preferred stabilizers are components which are naturally found in biological systems such as egg and soyabean lecithins or synthetic phosphatidyl cholines; or other surface active agents with low toxicity such as esters or ethers of fatty acids or fatty alcohols with polyoxyethylene compounds; ethers of fatty acids with polyoxyalkylated sorbitan or glycol; polyethoxylated soya oil and castor oil; and esters or ethers of carbohydrates with fatty acids or fatty alcohols, for instance polyoxyalkylated mono-, di- and triglycerides of saturated or unsaturated fatty acids, glycerides of soya oil and sucrose. Co-surfactants such as fatty acids or fatty alcohols with varying degrees of saturation and with 5 to 20 carbon atoms in the hydrocarbon chain or cholesterol may also be used. Especially preferred polymers or polyelectrolytes are polysaccharides, hyaluronic acid and poloxamers. Especially preferred are also stabilizers among proteins such as human serum albumin, gelatin. Synthetic proteins may have a preferred use due to lower immunogenic reactions.

Contrast media comprising a compound according to the invention suspended or emulsified as described above form a further aspect of the invention, as do processes for their preparation.

The contrast media according to the invention are suitable for use in methods of enhancing X-ray images of all parts of the human body, for example the vascular or lymphatic systems, and such methods form a yet further aspect of the invention. The suspensions or emulsions may be administered by the intravascular, preferably intravenous, route. However, their ability to become trapped in the reticulo-endothelial system makes them particularly useful in liver and spleen imaging.

Following entrapment in the reticulo-endothelial system and phagocytosis the compounds according to the invention are broken down into products which comprise on the one hand fatty acids, particularly natural fatty acids, and on the other hand harmless by-products such as the well known ionic or non-ionic iodinated contrast media represented by the group

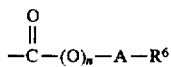

in the radicals of type (ii) defined above.

The following Examples illustrate the invention.

EXAMPLE 1

2-[1-(3,5-Diacetylamino-2,4,6-triiodobenzoyloxy)-ethoxycarbonl]-1,3-dipalmitoylglycerol (a) 1,3-Dipalmitoyl-1,3-dihydroxyacetone The title compound was prepared as described by Bently et al. in J. Org. Chem., 35, (1970), 2082.

Yield: 48%, mp 80°–81° C.

(b) 1,3-Dipalmitoylglycerol

The title compound was prepared as described by Bently et al. in J. Org. Chem., 35, (1970), 2082.

Yield: 69%, mp 71°–73° C.

(c) 2-(1-Chloroethoxycarbonyl)-1,3-dipalmitoylglycerol 1,3-Dipalmitoylglycerol (2.5 g, 4.39 mmol) and 1-chloroethyl chloroformate (1.26 g, 8.79 mmol) were dissolved in chloroform (50 ml). To this was added anhydrous pyridine dropwise. The reaction mixture was stirred at ambient temperature for 5 days, diluted with dichloromethane and extracted with 0.5N HCl solution. The organic layer was washed with a saturated sodium bicarbonate solution, washed again with water, dried over sodium sulphate and concentrated to dryness. The waxy residue was dried under reduced pressure and used without further purification.

Yield: 103%, mp 40°–43° C.

Calculated for $C_{38}H_{71}ClO_3$ %C 67.62; %H 10.40; %Cl 4.97

Found %C 67.57; %H 10.59; %Cl 5.25

$^1$H NMR (CDCl$_3$) δ: 6.42 (m, CHCl); 5.18 (m, C$\underline{H}$CH$_2$); 4.40–4.11 (m, CH$_2$OCO); 1.85 (d, C$\underline{H}_3$CH).

$^{13}$C NMR (CDCl$_3$) δ: 173.2, 173.1, 152.3 (3C, CO); 74.2 (CHCH$_2$); 61.8, 61.8 (CH$_2$OCO); 34.0 (CH$_2$CO) MS (CI, CH$_4$) 674, 552, 551, 548, 420, 418, 356, 312, 239, 237.

(d) Potassium 3,5-diacetylamino-2,4,6-triiodobenzoate

A suspension of 3,5-diacetylamino-2,4,6-triiodobenzoic acid (0.5 g, 0.81 mmol) in water (5 ml) was heated to 60° C. and an aqueous solution of KOH prepared by dissolving KOH (46 mg, 0.81 mmol) in water (2 ml) was added. A solution of 0.5N KOH was added dropwise to the suspension to adjust it to pH 7. Water was removed under reduced pressure to give a residue which was washed twice with ethanol and dried under reduced pressure.

Yield: 94%, mp 262° C.

(e) 2-[1-(3,5-Diacetylamino-2,4,6-triiodobenzoyloxy)-ethoxycarbonyl]-1,3-dipalmitoylglycerol 2-(1-Chloroethoxycarbonyl)-1,3-dipalmitoylglycerol (1.00 g, 1.43 mmol) and sodium iodide were dissolved in a solution of potassium 3,5-diacetylamino-2,4,6-triiodobenzoate (0.88 g, 1.35 mmol) in DMF (10 ml). After 5 days stirring at 50° C. 18-Crown-6 (40 mg, 0.15 mmol) was added to the mixture which was then stirred at 50° C. for a further 3 days. The reaction mixture was diluted with dichloromethane, washed 4 times with a saturated sodium bicarbonate solution, twice with water, dried over sodium sulphate and evaporated. The residue was purified by column chromatography on silica gel using heptane-ethyl acetate (1:2) as eluent.

Yield: 44%, mp 197°–202° C.

$^1$H NMR (CDCl$_3$) δ: 8.58, 8.54 (s, NH); 5.11 (m, CHCH$_2$); 4.42–4.15 (m. CH$_2$OCO); 1.71 (d, CH$_3$CH); 0.88 (t, CH$_3$CH$_2$).

$^{13}$C NMR (CDCl$_3$) δ: 173.8, (CH$_2$OCO); 152.3 (OCOO); 73.9 (CHCH$_2$); 61.8 (CH$_2$OCO); 34.0 (CH$_2$CO)

FAB-MS: 1253 [M+H]$^+$, 1209, 1083, 769.

EXAMPLE 2

1,3-Di[1-(3-acetylamino-5-(acetylmethylamino)-2,4,6-triiodobenzoyloxy)-ethoxycarbonyl]-2-stearoylglycerol (a) 1,3-Benzylidene-2-stearoylglycerol The title compound was prepared as described by Jensen et al. in Advances in lipid research, (1976), 213. (R. Paoletti) Academic Press, N.Y.

Yield: 76%, mp 73°–75° C.

(b) 2-Stearoylglycerol

The title compound was prepared by hydrolysis of 1,3-benzylidene-2-stearoylglycerol using the method described by Serdarevich et al. in J. Lip. Res., 7, (1966), 277.

Yield: 76%, mp 73°–75° C.

(c) 1,3-Di(1-chloroethoxycarbonyl)-2-stearoylglycerol

2-Stearoylglycerol (0.1 g, 0.28 mmol) was dissolved in dichloromethane (5 ml). To this was added anhydrous pyridine (49 mg, 0.62 mmol), followed by 1-chloroethyl chloroformate (89 mg, 0.62 mmol). The reaction mixture was allowed to proceed at ambient temperature overnight and worked up as described for 2-(1-chloroethoxycarbonyl)-1,3-dipalmitoylglycerol (Example 1c). The product was purified by recrystallization from ethanol.

Yield: 85%

$^1$H NMR (CDCl$_3$) δ: 6.40, (m, CHCl); 5.30 (m, CHCH$_2$) 4.50–4.25 (m, CH$_2$OCO); 1.83 (d, CH$_3$CH).

$^{13}$C NMR (CDCl$_3$) δ: 171.6, 151.7 (CO); 68.1 (CHCH$_2$); 66.1 (CH$_2$OCO); 34.5 (CH$_2$CO).

(d) Cesium 3-acetylamino-5-(acetylmethylamino)-2,4,6-triiodobenzoate

A suspension of 3-acetylamino-5-(acetylmethylamino)-2,4,6-triiodobenzoic acid (50.0 g, 79.62 mmol) in water (170 ml) was stirred and heated to 50° C. Cesium carbonate (12.8 g, 39.81 mmol) in water (20 ml) was added dropwise to the suspension until pH 7 was reached. Water was removed under reduced pressure to give a residue which was washed twice with ethanol and dried at 60° C. for 7 days.

Yield: 95%, mp 247° C. (decomp).

(e) 1,3-Di[1-(3-acetylamino-5-(acetylmethylamino)-2,4,6-triiodobenzoyloxy)-ethoxycarbonyl]-2-stearoylglycerol Cesium 3-acetylamino-5-(acetylmethylamino)-2,4,6-triiodobenzoate (0.20 g, 0.26 mmol) was suspended in toluene (10 ml) and DMF (20 ml). Toluene was evaporated in vacuo at 50° C. To the solution was added 1,3-di(1-chloroethoxycarbonyl)-2-stearoylglycerol (70 mg, 0.12 mmol) followed by a catalytic amount of potassium iodide (5 mg). After 12 hours stirring at 50° C. the reaction mixture was worked up as described in Example 1e. The product was separated by column chromatography on silica gel using ethyl acetate as eluant.

Yield: 55%, mp 123°–128° C.

$^1$H NMR (CDCl$_3$) δ: 8.02, (s, NH); 5.28 (m, CHCH$_2$) 4.42–4.27 (m, CH$_2$OCO); 1.74 (d, CH$_3$CH), 0.86 (t, CH$_3$CH$_2$).

$^{13}$C NMR (CDCl$_3$) δ: 173.8, (CH$_2$OCO); 152.5 (OCOO); 168.3 (ArCO); 170.0 (NCOCH$_3$); 93.3 (CHCH$_3$); 68.1 (CHCH$_2$); 65.9 (CH$_2$OCO); 34.1 (CH$_2$CO); 19.2 (CH CH$_3$)

FAB-MS 1755 [M+H]$^+$, 1629, 1501, 1375.

We claim:

1. A compound of formula (I)

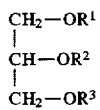

wherein R$^1$, R$^2$ and R$^3$ are independently selected from:
  (i) saturated or unsaturated fatty acyl groups;
  (ii) groups of formula

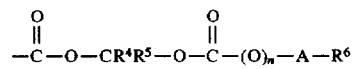

wherein R$^4$ and R$^5$ are independently selected from hydrogen atoms, C$_{1-4}$ alkyl groups and aryl groups, n represents the integers 0 or 1, A represents either a chemical bond or a straight or branched C$_{1-6}$ alkylene chain and R$^6$ is a group

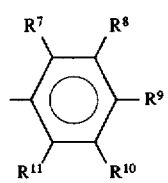

wherein at least three of R$^7$, R$^8$, R$^9$, R$^{10}$ and R$^{11}$ are iodine atoms and those of said groups R$^7$, R$^8$, R$^9$, R$^{10}$ and R$^{11}$ which are not iodine atoms are selected from hydrogen atoms, halogen atoms other than iodine, hydroxyl groups, C$_{1-6}$ alkoxy groups, amino groups, C$_{1-6}$ alkylthio groups, N-(C$_{1-6}$ alkyl)-amino groups, N-(C$_{1-6}$ alkanoyl)-amino groups, N-(C$_{1-6}$ alkyl)-N-(C$_{1-6}$ alkanoyl)-amino groups, carbamoyl groups and N-(C$_{1-6}$ alkyl)-carbamoyl groups, wherein any of the alkyl, alkylene, alkoxy, alkylthio, N-alkyl or N-acyl groups defined above may be substituted by one or more hydroxy or C$_{1-4}$ alkoxy groups;

provided that at least one of R$^1$, R$^2$ and R$^3$ is a fatty acyl group and at least one of R$^1$, R$^2$ and R$^3$ is a radical containing an iodinated phenyl group as defined above.

2. A compound as claimed in claim 1 wherein $R^6$ is a 2,4,6-triiodophenyl group or a substituted 2,4,6-triiodophenyl group as defined in claim 1.

3. A compound as claimed in claim 1 wherein n represents the integer 0 and A represents a chemical bond.

4. A compound as claimed in claim 1 wherein at least one of $R^1$, $R^2$ and $R^3$ is a $C_{16-18}$ fatty acyl group.

5. A compound as claimed in claim 1 wherein at least one of $R^7$, $R^8$, $R^9$, $R^{10}$, and $R^{11}$ is an N-($C_{1-6}$alkanoyl)-amino, N-($C_{1-6}$-alkyl)-N-($C_{1-6}$alkanoyl)-amino, N-(hydroxy substituted $C_{1-6}$ alkyl)-N-($C_{1-6}$alkanoyl)-amino, carbamoyl, N-($C_{1-6}$alkyl)-carbamoyl, N-(hydroxy substituted $C_{1-6}$alkyl)-carbamoyl, di-N-($C_{1-6}$alkyl)-carbamoyl, N-($C_{1-6}$-alkyl)-N-(hydroxy substituted $C_{1-6}$alkyl)-carbamoyl or di-N-(hydroxy substituted $C_{1-6}$alkyl)-carbamoyl group.

6. An X-ray contrast medium comprising a compound as claimed in claim 1 suspended or emulsified in a physiologically acceptable liquid, wherein the suspended or emulsified compound has a particle or droplet size respectively of 0.01 to 10 μm.

7. A method of enhancing an X-ray image of a human subject comprising intravascular administration to said subject, prior to imaging, of a medium as claimed in claim 6.

8. An X-ray contrast medium comprising a compound as claimed in claim 2 suspended or emulsified in a physiologically acceptable liquid, wherein the suspended or emulsified compound has a particle or droplet size respectively of 0.01 to 10 μm.

9. An X-ray contrast medium comprising a compound as claimed in claim 5 suspended or emulsified in a physiologically acceptable liquid, wherein the suspended or emulsified compound has a particle or droplet size respectively of 0.01 to 10 μm.

10. An X-ray contrast medium comprising a compound as claimed in claim 3 suspended or emulsified in a physiologically acceptable liquid, wherein the suspended or emulsified compound has a particle or droplet size respectively of 0.01 to 10 μm.

11. An X-ray contrast medium comprising a compound as claimed in claim 4 suspended or emulsified in a physiologically acceptable liquid, wherein the suspended or emulsified compound has a particle or droplet size respectively of 0.01 to 10 μm.

12. A method of enhancing an X-ray image of a human subject comprising intravascular administration to said subject, prior to imaging, a medium as claimed in claim 8.

13. A method of enhancing an X-ray image of a human subject comprising intravascular administration to said subject, prior to imaging, a medium as claimed in claim 9.

14. A method of enhancing an X-ray image of a human subject comprising intravascular administration to said subject, prior to imaging, a medium as claimed in claim 10.

15. A method of enhancing an X-ray image of a human subject comprising intravascular administration to said subject, prior to imaging, a medium as claimed in claim 11.

* * * * *